(12) United States Patent
McAuley

(10) Patent No.: US 7,824,397 B2
(45) Date of Patent: Nov. 2, 2010

(54) OCCLUSION APPARATUS

(75) Inventor: Steven A. McAuley, Chanhassen, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1210 days.

(21) Appl. No.: 11/207,271

(22) Filed: Aug. 19, 2005

(65) Prior Publication Data

US 2007/0043344 A1 Feb. 22, 2007

(51) Int. Cl.
*A61B 18/04* (2006.01)
(52) U.S. Cl. .......................... 606/27; 606/49
(58) Field of Classification Search .................. 606/41, 606/49, 27
See application file for complete search history.

(56) References Cited

U.S. PATENT DOCUMENTS

| | | | |
|---|---|---|---|
| 5,769,790 A | 6/1998 | Watkins et al. | |
| 5,865,791 A * | 2/1999 | Whayne et al. | 604/500 |
| 5,919,200 A | 7/1999 | Stambaugh et al. | |
| 5,944,738 A | 8/1999 | Amplatz et al. | |
| 6,007,514 A | 12/1999 | Nita | |
| 6,024,718 A | 2/2000 | Chen et al. | |
| 6,152,144 A * | 11/2000 | Lesh et al. | 128/898 |
| 6,378,501 B1 | 4/2002 | Hisato et al. | |
| 6,458,100 B2 | 10/2002 | Roue et al. | |
| 6,482,224 B1 | 11/2002 | Michler et al. | |
| 6,645,225 B1 | 11/2003 | Atkinson | |
| 6,650,923 B1 | 11/2003 | Lesh et al. | |
| 6,656,136 B1 | 12/2003 | Weng et al. | |
| 6,716,184 B2 | 4/2004 | Vaezy et al. | |
| 6,755,790 B2 | 6/2004 | Stewart et al. | |
| 6,776,784 B2 | 8/2004 | Ginn | |
| 7,052,492 B2 * | 5/2006 | Swanson et al. | 606/32 |
| 2002/0173688 A1 | 11/2002 | Chen et al. | |
| 2002/0183787 A1 | 12/2002 | Wahr et al. | |
| 2003/0013971 A1 | 1/2003 | Makin et al. | |
| 2003/0045901 A1 | 3/2003 | Opolski | |
| 2003/0050665 A1 | 3/2003 | Ginn | |
| 2003/0144694 A1 | 7/2003 | Chanduszko et al. | |
| 2003/0181945 A1 | 9/2003 | Opolski et al. | |
| 2003/0191495 A1 | 10/2003 | Ryan et al. | |
| 2003/0208232 A1 | 11/2003 | Blaeser et al. | |
| 2003/0225421 A1 | 12/2003 | Peavy et al. | |
| 2004/0073242 A1 | 4/2004 | Chanduszko | |
| 2004/0087968 A1 | 5/2004 | Core | |
| 2004/0092973 A1 | 5/2004 | Chanduszko | |
| 2004/0093017 A1 | 5/2004 | Chanduszko | |
| 2004/0098121 A1 | 5/2004 | Opolski | |
| 2004/0127855 A1 | 7/2004 | Core | |
| 2004/0127917 A1 | 7/2004 | Ginn | |
| 2004/0133236 A1 | 7/2004 | Chanduszko | |

(Continued)

OTHER PUBLICATIONS

International Search Report, Dec. 1, 2006, 6 pgs.

*Primary Examiner*—Lee S Cohen
(74) *Attorney, Agent, or Firm*—Brooks, Cameron & Huebsch, PLLC

(57) ABSTRACT

Methods, apparatus, and systems for occluding a left atrial appendage are provided. One embodiment includes an elongate body having a tissue apposition member extendably positioned within a lumen of the elongate body to appose tissue of the LAA. An energy emitting device coupled to the elongate body can be used for emitting high intensity focused ultrasound to the tissues to fuse the tissues.

3 Claims, 14 Drawing Sheets

U.S. PATENT DOCUMENTS

| | | |
|---|---|---|
| 2004/0176788 A1 | 9/2004 | Opolski |
| 2004/0176797 A1 | 9/2004 | Opolski |
| 2004/0176799 A1 | 9/2004 | Chanduszko et al. |
| 2004/0193147 A1 | 9/2004 | Malecki et al. |
| 2004/0230185 A1 | 11/2004 | Malecki et al. |
| 2004/0243122 A1 | 12/2004 | Auth et al. |
| 2004/0267191 A1 | 12/2004 | Gifford, III et al. |
| 2004/0267306 A1 | 12/2004 | Blaeser et al. |
| 2005/0021016 A1 | 1/2005 | Malecki et al. |
| 2005/0034735 A1 | 2/2005 | Deem et al. |
| 2005/0043759 A1 | 2/2005 | Chanduszko |
| 2005/0059983 A1 | 3/2005 | Opolski et al. |
| 2005/0070923 A1 | 3/2005 | McIntosh |
| 2005/0070952 A1 | 3/2005 | Devellian |
| 2005/0080406 A1 | 4/2005 | Malecki et al. |
| 2005/0080430 A1 | 4/2005 | Wright, Jr. et al. |
| 2005/0085843 A1 | 4/2005 | Opolski et al. |
| 2005/0101984 A1 | 5/2005 | Chanduszko et al. |
| 2005/0131401 A1 | 6/2005 | Malecki et al. |
| 2005/0131460 A1 | 6/2005 | Gifford, III et al. |

\* cited by examiner

OCCLUSION APPARATUS

FIELD OF THE INVENTION

The present disclosure relates generally to apparatus, systems, and methods for use in the human body, more particularly to apparatus, systems, and methods to close an opening of a left atrial appendage in the heart.

BACKGROUND

The human heart is divided into four chambers. These include the right atrium, the right ventricle, the left atrium, and the left ventricle. The right atrium and right ventricle are divided from the left atrium and left ventricle by a muscular wall called the septum. The atrial septum is the wall separating the atria and the ventricular septum is the wall separating the ventricles.

Both the right and left atrium have a pouchlike structure attached to the atrium, which is called the right atrial appendage and the left atrial appendage (LAA). The LAA is the remnant of the original embryonic left atrium that develops during the third week of gestation. The LAA is a long, tubular, hooked structure which is usually crenellated and has a narrow junction with the venous component of the atrium.

In adults, there are no known uses for the left and right atrial appendages, like the appendix in the intestines. In the normal heart, the appendages contract, along with the rest of the atrial muscle and the blood moves in and out of the atrial appendages. In atrial fibrillation, there is a lack of synchronous or uniform contraction of the atrium muscle. Thus, the blood in the appendages remains dormant and does not move. In the right atrium, this has not been a health problem. In the LAA however, dormant blood can cause health problems. When the blood remains dormant in the LAA, thrombus has a tendency to form. In some patients, thrombus in the LAA can leave and travel within the cardiovascular system. In some instances, thrombus can travel to the brain and result in a stroke.

DETAILED DESCRIPTION

Embodiments of the present disclosure are directed to methods, apparatus, and systems for apposing tissues of the left atrial appendage and fusing the tissues to occlude the opening of the LAA. For example, in various embodiments, apposing and fusing tissues of the LAA can be accomplished through the use of a catheter delivered to the left atrium. In various embodiments, once the catheter is properly positioned within the left atrium, a tissue apposition member can be extended from the catheter and an apposition arm positioned within the tissue apposition member can be used to manipulate the tissue of the LAA so as to bring the tissue together. In another embodiment, once the catheter is properly positioned within the left atrium, a closure sheath can be retracted to release an apposition arm held in compression by the closure sheath in a collapsed state such that the apposition arm can spring toward an expanded state to engage tissue and bring the tissue together. In various embodiments, an energy emitting device can be used to apply ultrasound focused to a high intensity to the tissues so as to fuse the tissues together and close the LAA.

In various embodiments, a system can include the catheter including various components (e.g., tissue apposition member and apposition arms) therein. The system can also include an energy emitting device configured to emit focused ultrasound at a high intensity to tissues of the LAA. A targeting device configured to locate and/or create a target (e.g., tissues of the LAA) and guide the focused ultrasound to the target can also be included in the system. In such a system, focused ultrasound can be guided to the target from within the human body or from outside the human body.

As will be discussed herein, in the various embodiments of the present disclosure, tissues can be brought together before, during, and/or after applying energy to the tissues. The use of focused ultrasound and other types of energy (e.g., RF energy) on tissues denatures the collagen in the tissue. Tissues that undergo denaturization will tend to renature. If tissues brought together remain in contact while they renature, the collagen in the tissues brought together will effectively combine to fuse the once separated tissues together.

The method, apparatus, and system embodiments described herein are illustrated with reference to fusing tissue of the LAA to occlude an opening of the LAA. However, the method, apparatus, and system embodiments can also be used to fuse other tissues and thus, occlude other openings. For example, using the various method, apparatus, and system embodiments described herein, various defective occlusions such as patent ductus arteriosus (PDA), atrial septal defects (ASDs), and ventricular septal defects (VSDs) can be occluded.

Figure 1:
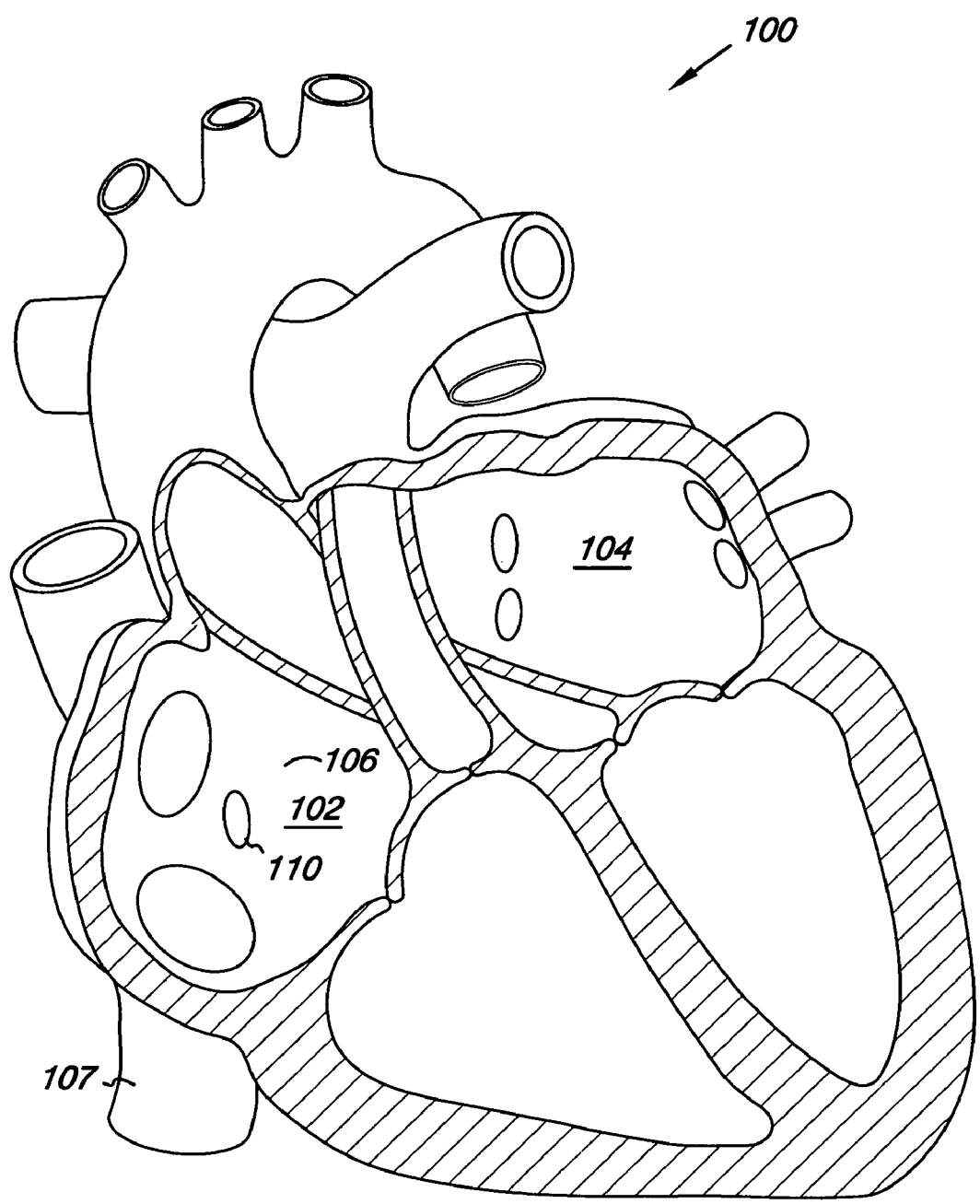
FIG. 1 illustrates a perspective view of the heart is shown.

In FIG. 1, a perspective view of the heart 100 is shown. As noted above, the heart 100 is divided into four chambers, which are referred to herein as the right atrium 102, a right ventricle, a left atrium 104 and a left ventricle. Heart 100 also includes a septal wall 106 that divides the four chambers of the heart 100. The portion of the septal wall dividing the left and right atriums 102 and 104 is called the interatrial septum. The portion of the septal wall 106 dividing the left and right ventricle is called the ventricular septum. The fossa ovalis 110 is an oval depression on the septal wall 106 of the interatrial septum 108, and corresponds to the situation of the foramen ovale (i.e., the communication between the right and left atria in the fetal heart). As will be discussed herein, the various apparatus, system, and method embodiments utilized to fuse the LAA can gain access to the LAA by entering the right atrium and advancing through tissue adjacent to the fossa ovalis 110 to enter the left atrium or advancing through a passage adjacent to the fossa ovalis 510.

Figure 2:
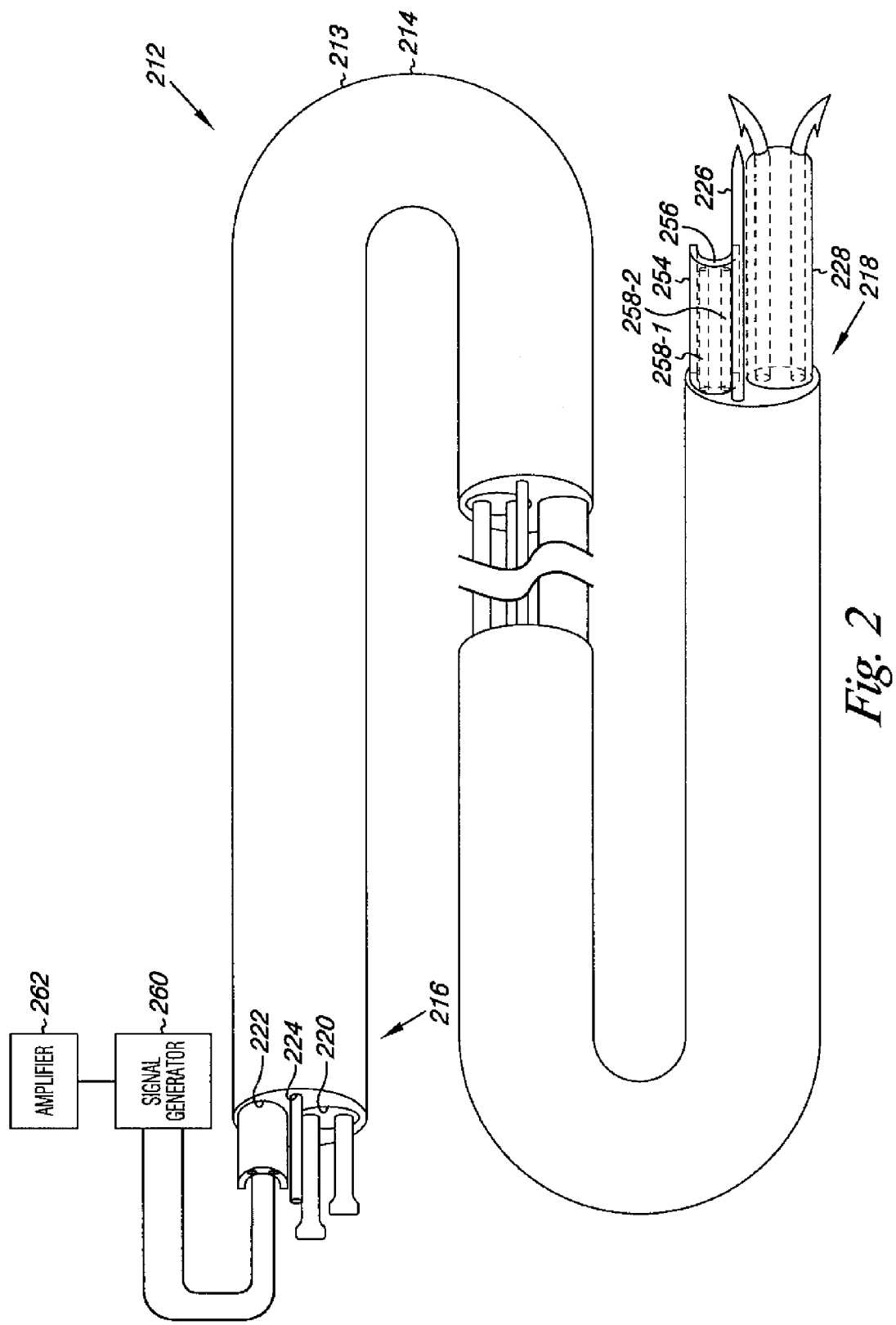
FIG. 2 illustrates an embodiment of an occlusion apparatus according to the teachings of the present disclosure.

FIG. 2 illustrates an embodiment of an occlusion apparatus 212 according to the teachings of the present disclosure. In various embodiments, the occlusion apparatus 212 includes a catheter 213 having an elongate body 214 with a proximal end 216 a distal end 218. In various embodiments, the elongate body 214 can include a number of lumens. In the embodiment of FIG. 2, the elongate body 214 includes a first lumen 220, a second lumen 222, and a guidewire lumen 224. In various embodiments, each lumen 220, 222, and 224 can extend from the proximal end 220 toward the distal end 222 of the elongate body 214. In various embodiments, each lumen 220, 222, and 224 can include various configurations. For example, in some embodiments, the guidewire lumen 224, the first lumen 220 and the second lumen 224 can include a tri-lumen configuration within the catheter 213, as shown in FIG. 2. In other embodiments, the lumens of the catheter can include a coaxial lumen design (e.g., lumen within a lumen).

In various embodiments, the first lumen 220, the second lumen 222, and the guidewire lumen 224 of the elongate body 214 can house a number of components of the occlusion apparatus 212. For example, in various embodiments, the guidewire lumen 224 can receive a guidewire 226 for positioning the occlusion apparatus 212 within a heart chamber e.g., a left atrium of a patient. In some embodiments, the guidewire can include a lumen and a pointed tip for piercing tissue adjacent the fossa ovalis to gain entry to the left atrium and to inject contrast media into the left atrium, as will be discussed herein with respect to FIG. 5A.

In various embodiments, the first lumen 220 of the elongate body 214 can include a tissue apposition member 228. The tissue apposition member 228 can be extendably positioned at least partially within the first lumen 220 of the elongate body 214. In various embodiments, the tissue apposition member 228 can include various components that can be used to bring tissues of a left atrial appendage together, as discussed below with respect to FIGS. 3A-3G.

FIGS. 3A-3G illustrate various embodiments of the tissue apposition member 328 of the present disclosure. In various embodiments of FIGS. 3A-3G, the tissue apposition member 328 includes an elongate body 330 having a proximal end 332 and a distal end 334. In various embodiments, the elongate body 330 can include various geometric shapes including, but no limited to, circular, ovular, polygonal, and irregular geometric shapes. The elongate body 330 of the tissue apposition member 328 can be constructed from a number of materials. In some embodiments, the materials used to form the elongate body can be rigid, semi-flexible, or flexible. Examples of materials include, but are not limited to, metal, metal alloys, shape memory metals, polymeric materials including shape memory polymers, natural and synthetic materials, and others.

Figures 3A, 3B:
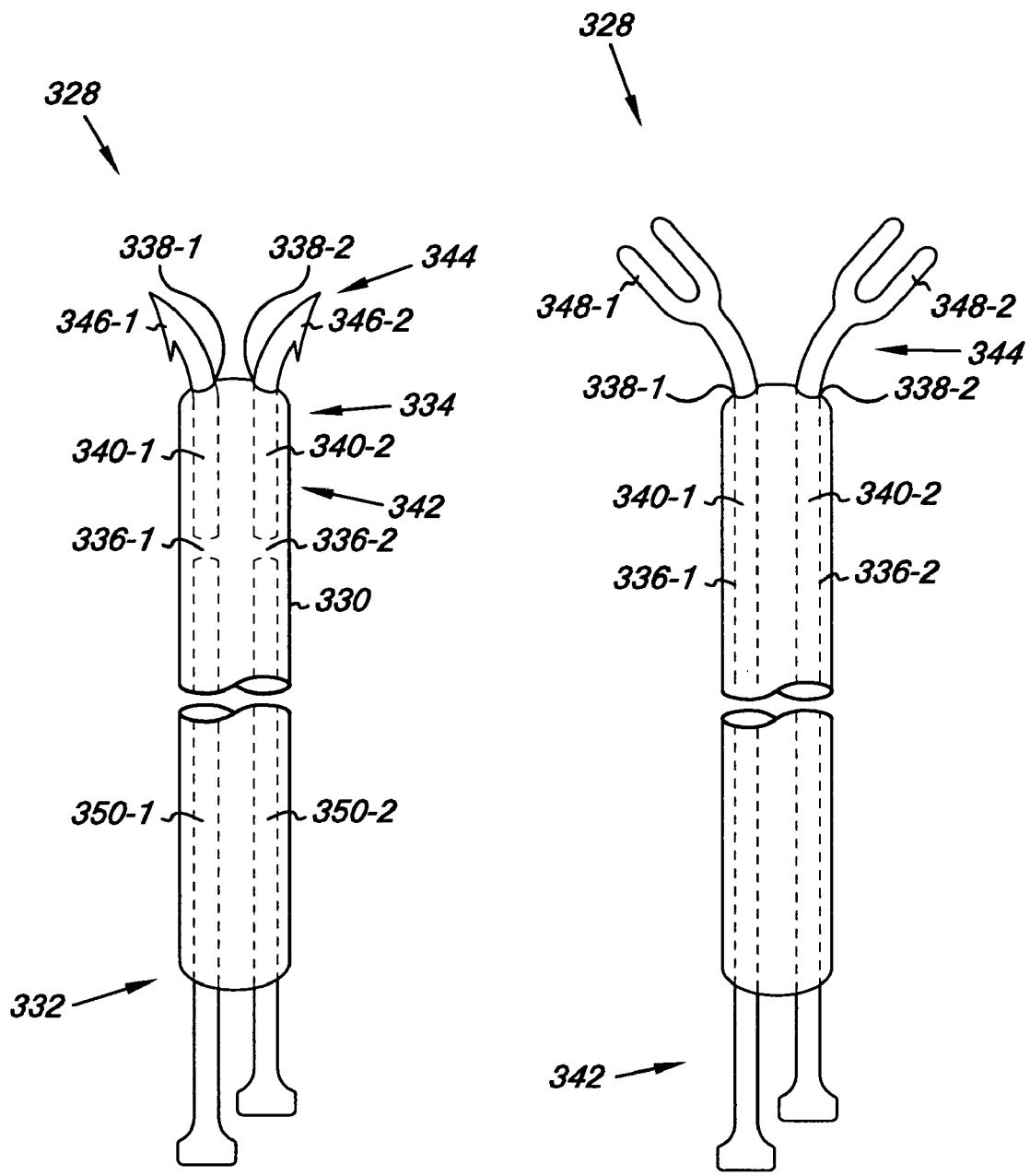
FIGS. 3A-3G illustrates various embodiments of a tissue apposition member according to the teachings of the present disclosure.
Figures 3C, 3D:
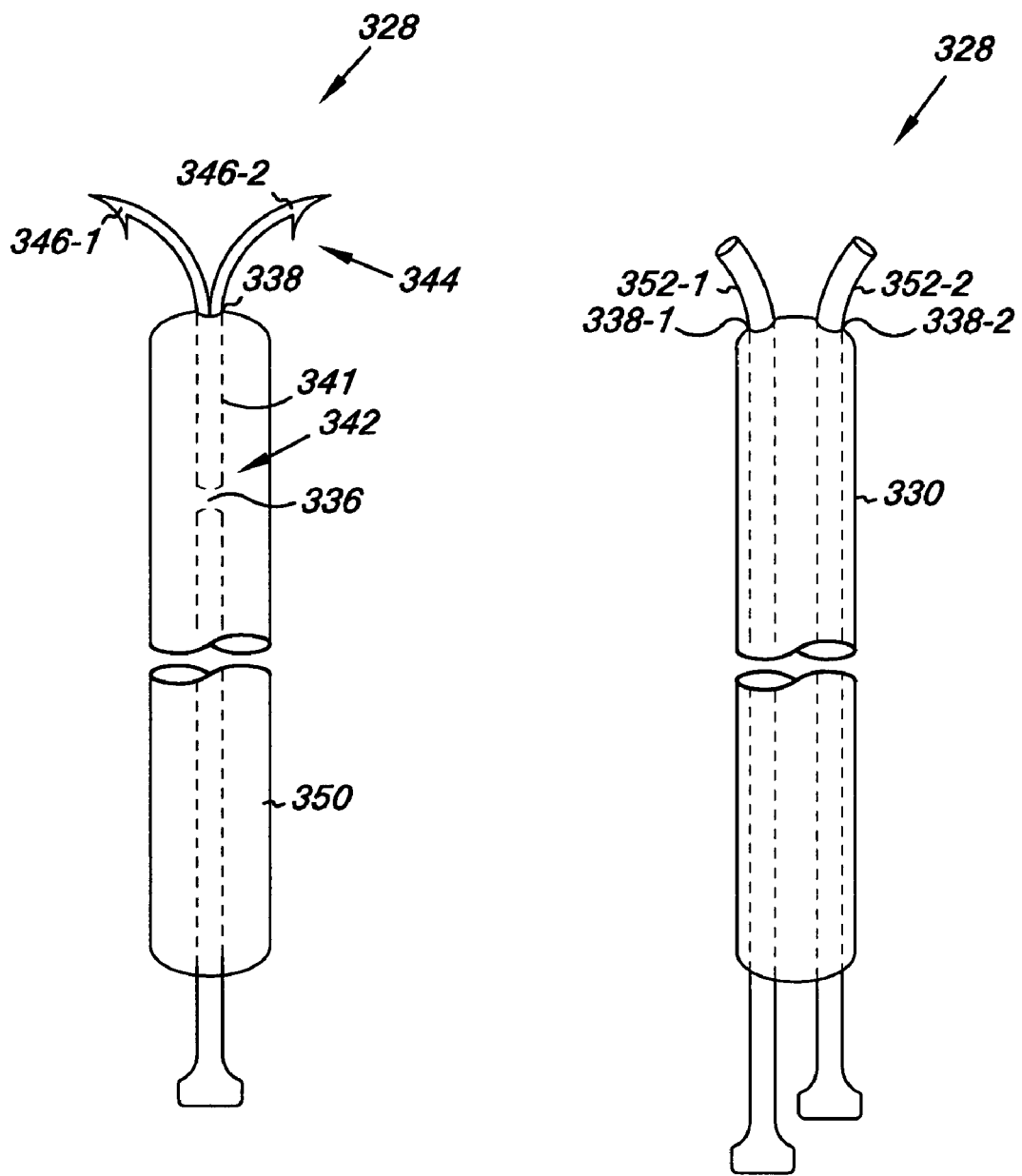

In various embodiments, the tissue apposition member 328 can include a number of lumens extending between the proximal and the distal end 332 and 334. In some embodiments, the tissue apposition member 328 can include a single lumen, and in other embodiments, the tissue apposition member can include two or more lumens. In various embodiments, the lumens of the tissue apposition member can include an independent configuration, e.g., a dual lumen configuration as shown in the embodiment of FIGS. 3A, 3B, and 3D. In some embodiments, the lumens of the tissue apposition member 328 can include a coaxial configuration.

The lumens of the tissue apposition member can house various components that can be extended, and/or retracted within the tissue apposition member 328 through one or more openings in the tissue apposition member 328. In some embodiments, components of the tissue apposition member can be released from the tissue apposition member 328 after they have engaged tissue within the human body. In addition, in various embodiments, components can be used to manipulate tissues within the human body, e.g., to bring tissues together.

In various embodiments of FIGS. 3A-3G, components can include apposition arms (e.g., apposition arms 340-1 and 340-2 illustrated in FIG. 3A). In various embodiments, the apposition arms can be positioned within a lumen of the tissue apposition member 328 in a manner that allows them to engage various tissues, such as tissue of an LAA, through various engaging mechanisms such as pushing, springing, expanding, etc., and other engaging mechanisms. For example, in various embodiments of FIGS. 3A and 3C, deployment rods 350, 350-1 and 350-2 can be utilized to push apposition arms 340-1 and 340-2 within lumens 336-1 and 336-2 and through opening 338-1 and 338-2 to engage tissue of an LAA.

Figure 3G:
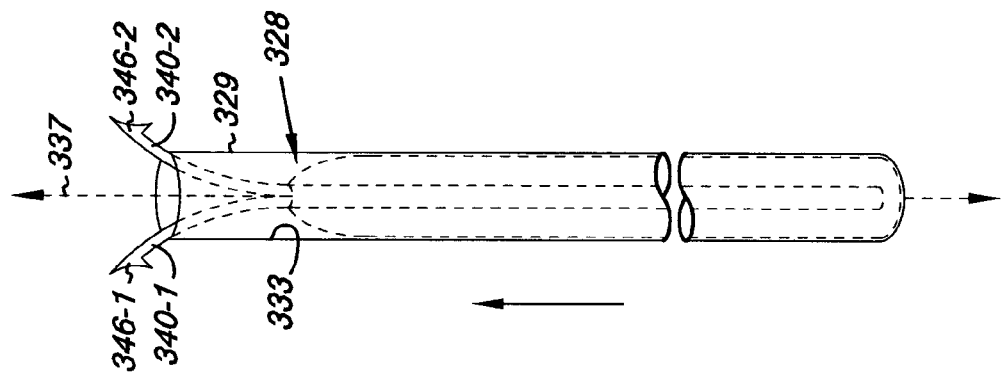
Figure 3F:
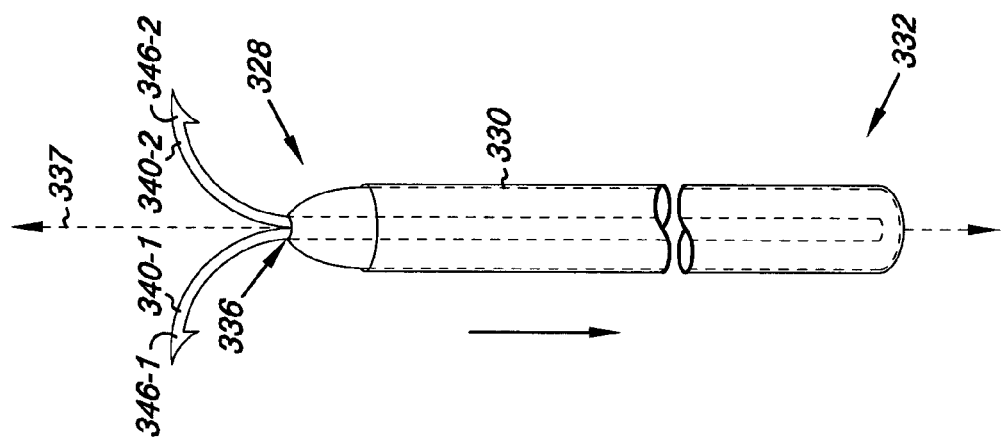
Figure 3E:
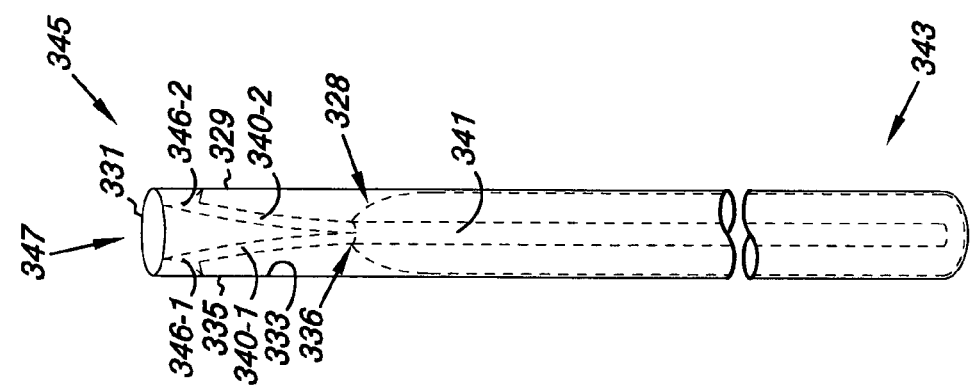

In another example, apposition arms of tissue apposition member 328, such as apposition arms 340-1 and 340-2 illustrated in FIG. 3E, can be formed of a resilient material and compressed within lumen 331 of the a closure sheath 329. In such embodiments, when the compression is released, such as when the closure sheath 329 is retracted, the apposition arms 340-1 and 340-2 are no longer held in compression and can spring toward a biased direction radially from a longitudinal axis of the tissue apparatus member 328. These and other embodiments will be discussed in more detail in FIGS. 3A-3E and 5A-5F.

According to various embodiments illustrated in FIGS. 3A-3E, apposition arms can include a variety of predefined shapes and sizes that allow for the apposition arms to engage tissue, such as tissue of the LAA. In various embodiments, engaging tissue can include clamping, grasping, gripping, hooking, piercing, lodging, catching, vacuuming, pushing, pulling, and/or trapping such that the tissue can be brought together or otherwise manipulated. In various embodiments, engaging tissue can also include various engaging mechanisms such as springing, pushing, and pulling, among others.

For example, n various embodiments of FIG. 3A, the tissue apposition member 328 can include a first lumen 336-1 and a second lumen 336-2 in communication with a first opening 338-1 and a second opening 338-2. The first and second lumen 336-1 and 336-2 extend from the proximal end 332 toward the distal end 334 of the tissue apposition member 328. In various embodiments, the first and second lumen 336-1 and 336-2 can be designed to accommodate a number of components, e.g., apposition arms 340-1 and 340-2 and deployment rods 350-1 and 350-2.

In various embodiments, the deployment rods 350-1 and 350-2 can be formed of a resilient material that allows the deployment rods to flex, bend, and rotate when deployed from the distal end of the tissue apposition member, as will be discussed below with respect to FIGS. 5A-5E. The deployment rods can be releasably coupled to the apposition arms 340-1 and 340-2 and can be used by an operator to manipulate the apposition arms 340-1 and 340-2. In various embodiments, manipulating the apposition arms 340-1 and 340-2 can include engaging the tissues of the LAA by pushing the apposition arms such that hooking structures 346-1 and 346-2 at the distal end 344 of the apposition arms 340-1 and 340-2 pierce and hook the tissues. Once engaged, the apposition arms 340-1 and 340-2 can be pulled by an operator to bring the tissues together.

In another embodiment, the tissues of the LAA can be brought together by sliding a closure sheath 329 along a longitudinal axis of the tissue apposition member 328 to draw the engaged apposition members 340-1 and 340-2 together and thereby, bring tissue engaged to the apposition arms 340-1 and 340-2 together, as will be discussed with respect to FIGS. 3E-3G, and 6A-6C.

In various embodiments, it may be desirable to leave the apposition arms 340-1 and 340-2 within engaged tissue. In such embodiments, the deployment rods 350-1 and 350-2 can be used to release the apposition arms 340-1 and 340-2 from the tissue apposition member 328 such that the apposition arms 340-1 and 340-2 remain lodged within the tissue.

FIG. 3B illustrates another embodiment of the tissue apposition member 328. In the embodiment of FIG. 3B, the tissue apposition member 328 includes the first and second apposition arms 340-1 and 340-2. The apposition arms 340-1 and 340-2 illustrated in FIG. 3B include a grasping structures 348-1 and 348-2 at the distal end 344 of the apposition arms 340-1 and 340-2. In various embodiments of FIG. 3B, the apposition arms 340-1 and 340-2 can extend radially from the tissue apposition member 328 through openings 338-1 and 338-2. The grasping structure 348 allows the apposition arms 340-1 and 340-2 to grasp the tissues of the LAA such that the tissue can be pulled by an operator manipulating the apposition arms 340-1 and 340-2 to bring the tissues together. Similarly, in various embodiments, the apposition arms 340-1 and 340-2 can bring tissue together by extending a closure sheath longitudinally over the tissue apposition member to draw the apposition arms together 340-1 and 340-2, as will be discussed in more detail with respect to FIGS. 5A-5F.

FIG. 3C illustrates an embodiment of the tissue apposition member 328 having a lumen 336 and two apposition arms 340-1 and 340-2 that diverge at a base 341 of the apposition arms 340-1 and 340-2. In various embodiments, the apposition arms 340-1 and 340-2 can be extendably and releasably positioned within the lumen 336. In the embodiment of FIG. 3C, the apposition arms 340-1 and 340-2 diverge from the base 342 and extend radially relative to a longitudinal axis of the tissue apposition member 328. In this embodiment, the apposition arms 340-1 and 340-2 include hooking structures 346-1 and 346-2 at the distal end 344 of the apposition arm 340. In various embodiments, the apposition arms 340-1 and 340-2 can be releasably coupled to the base 341. In such embodiments, the apposition arms can be released from the base 341 such as when they have engage tissue and are to be left within the engaged tissue.

In various embodiments, the apposition arms 340-1 and 340-2 can be manipulated using a deployment rod 350 to engage tissue of the LAA by piercing and hooking the tissue with the first and second hooking structures 346-1 and 346-2 to bring them together. In some embodiments, the apposition arms can be formed of a resilient material that provides the apposition arms with spring like properties that allow the hooking structures to pierce and hook tissue of the LAA without manipulating the apposition arms with the deployment rod 350, as will be discussed with respect to FIGS. 3E-3G.

FIGS. 3E-3G illustrates an embodiment of the tissue apposition member similar to tissue apposition member 328 illustrated in FIG. 3C. In various embodiments, tissue apposition member 328 can be slidably positioned within a closure sheath 329. In various embodiments, the closure sheath 329 can include a proximal end 343 and a distal end 345. In various embodiments, the distal end 345 of the closure sheath 329 can include an opening 347 in communication with a lumen 331 of the closure sheath 329. In various embodiments, the closure sheath can be formed to include a lubricous inner surface 333 and outer surface 335 to provide for the slidability of the closure sheath 329 within a lumen of a catheter and along an outer surface of the tissue apposition member 328.

As shown in FIG. 3E, the apposition arms 340-1 and 340-2 include the base 341. The base 341 of the apposition arms 340-1 and 340-2 is positioned within lumen 336 of the tissue apposition member 328 and can extend along the length of the tissue apposition member 328 from the distal end 334 to the proximal end 332. In some embodiments, the base 342 can extend from the lumen 336 at the proximal end 332 such that the apposition arms 340-1 and 340-2 can be manipulated by an operator. In various embodiments, the apposition arms 340-1 and 340-2 and hooking structures 346-1 and 346-2 are positioned within lumen 331 of the closure catheter 329. In this embodiment, the apposition arms 340-1 and 340-2 are in a collapsed state (i.e., held in compression by inner surface 333 of lumen 331 of the closure sheath 329).

As shown in FIG. 3F, the apposition arms 340-1 and 340-2 are in an expanded state. In various embodiments, the closure sheath 329 can be retracted toward the proximal end 332 of the elongate body 330 of the tissue apposition member 328 to release the apposition arms 340-1 and 340-2. When the apposition arms are released 340-1 and 340-2, they spring radially away from a longitudinal axis 337 of the tissue apposition member 328 in various directions. In such embodiments, the spring like properties of the apposition arms 340-1 and 340-2 can engage tissue of the LAA by piercing and hooking the tissue with the hooking structures 346-1 and 346-2 when the apposition arms 340-1 and 340-2 are released adjacent to or proximal to such tissues.

Referring now to FIG. 3F, in various embodiments, the closure sheath 329 can be used to draw apposition arms 340-1 and 340-2 together by sliding the closure sheath 329 along the longitudinal axis 337 of the tissue apposition member 328 toward the hooking structures 346-1 and 346-2 such that the inner surface 333 of the closure sheath 329 compresses the apposition arms 340-1 and 340-2 toward each other. In various embodiments, the longitudinal axis 337 of the tissue apposition member 328 can provide a guide for the closure sheath 329 to draw the apposition arms 340-1 and 340-2 together. In such embodiments, tissue of the LAA engaged to the apposition arms can be brought together, as will be discussed in FIGS. 6A-6C.

In various embodiments, the apposition arms can be formed of various materials that provide spring like (i.e., elastic) properties to the apposition arms. Examples of suitable materials for forming the apposition arms can include, but are not limited to, metals, metal alloys, and/or polymer materials. Specific examples of such materials can include shape memory metals such as Nitinol, linear-elastic Nitinol, super-elastic Nitinol, shape memory polymers, medical grade stainless steel (e.g., 316L), titanium, tantalum, platinum alloys, niobium alloys, cobalt alloys, alginate, MP35N, aluminum alloys, chromium alloys, copper alloys, vanadium alloys, or combinations thereof. Examples of plastics can include shape memory plastics, polymers, and thermoplastic materials. Other materials are also contemplated.

These materials can allow for forming and setting the expanded state in the arms 340-1 and 340-2 that can resiliently flex to be compressed within the lumen 331 of the closure sheath 329 and then spring toward their expanded shape when the arms 340-1 and 340-2 are released from the lumen 331, such as when the closure sheath 329 is retracted.

In various embodiments, the apposition arms, can be releasably coupled to the tissue apposition member 328 such that they can be released from the tissue apposition member 328 and left in the human body. In such embodiments, the apposition arms can be released using a number of mechanical or chemical mechanisms. For example, in various embodiments, a deployment rod can be coupled to an apposition arm by threading the deployment rod to the apposition arm. In such embodiments, the deployment rod can release the apposition arm by unthreading the apposition arm. In another embodiment, the deployment rod can be coupled to the apposition arm by a chemical adhesive. In such an embodiment, the deployment rod can be released from the apposition arm by heating the adhesive and/or applying a sufficient force to the deployment such that the chemical bond holding the deployment rod to the apposition arm breaks.

In embodiments where the apposition arms are released from the tissue apposition member and left behind in the human body, the apposition arms can be formed of bioabsorbable materials that can degrade and be absorbed by the human body after a period of time. Examples of biodabsorbable materials include, but are not limited to, polycarboxylic acid, polyanhydrides including maleic anhydride polymers; poly-orthoesters; poly-amino acids; polyethylene oxide; polyphosphazenes; polyactic acid, polyglycolic acid and copolymers and copolymers and mixtures thereof such as poly(L-lactic acid) (PLLA), poly (D,L,-lactide), poly(lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocaronates, and polydimethyltrimethylcarbonates; cyanoacrylate; calcium phosphates; polyglycosaminoglycans; macromolecules such as polysaccharides (including hyaluronic acid, cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

Referring now to FIG. 3D, another embodiment of the tissue apposition member 328 is illustrated. In the embodiment of FIG. 3D, the tissue apposition member 328 includes a first suction arm 352-1 and a second suction arm 352-2 that can be extendably positioned within the first and second lumens 336-1 and 336-2 of the tissue apposition member 328. In the embodiment of FIG. 3D, the suction arms 352-1 and 352-2 can extend radially from the tissue apposition member 328 through openings 338-1 and 338-2. In such embodiments, suction arms 352-1 and 352-2 can be positioned adjacent tissues of the LAA and a vacuum can be applied to the tissues to cause the tissues to attach to the suction arms 352-1 and 352-2. Once the tissues are attached, an operator can manipulate the suction arms, e.g., retract the suction arms, to bring the tissues together or otherwise maneuver their position, as will be discussed herein.

In various embodiments, the suction arms 352-1 and 352-2 can be attached to a vacuum element located outside the human body which can be used to create the vacuum. In various embodiments, the suction arms 352-1 and 352-2 can be formed of a variety of materials including, but not limited to, metal, metal alloys, shape memory metals, polymeric materials including shape memory polymers, natural and synthetic materials, and others.

Referring again to FIG. 2, the elongate body 214 of catheter 213 includes the second lumen 222. Second lumen 222 extends from the proximal 216 end to the distal end 218 of the catheter 213. In various embodiments, the energy emitting device can be operatively coupled to the catheter and can be extendably positioned within the second lumen 222. As used herein, operatively coupled means that the energy emitting device 254 includes the necessary components, e.g., power source, conductors, software, computer, and other components that can be connected to the energy emitting device in a wireless and/or wired fashion to allow the energy emitting device to properly function. As used herein, an energy emitting device 254 is a device that can emit various types of energy including, but not limited to, high intensity focused ultrasound (HIFU), low intensity ultrasound (e.g., imaging ultrasound), RF energy, cryogenic energy, laser, resistive heat energy, and microwave. In various embodiments, the energy emitting device can be designed to emit more than one type of energy. For example, in some embodiments, energy emitting device 254 can be configured to emit high intensity focused ultrasound and low intensity ultrasound. As used herein, energy emitting devices 254 may have a number of different configurations, which can depend on the type of device, its placement location relative to the occlusion apparatus (e.g., on or physically separate from the occlusion apparatus), as well as its intended operational methods. For example, in some embodiments, the energy emitting device 254 can include a high intensity focused ultrasound (HIFU) transducer operatively coupled to the occlusion apparatus 212, as shown in the embodiment of FIG. 2. In such embodiments, the energy emitting device 254 is configured to emit HIFU to a target from within the human body. In other embodiments, such as in the embodiment illustrated in FIG. 4, the energy emitting device 254 is configured to emit the HIFU from outside the human body to a target located inside the human body.

According to various embodiments, the HIFU transducer 256 can be formed of a number of piezoelectric materials that can deform and emit HIFU when an electrical potential is supplied to the HIFU transducer 256. The HIFU transducer can include insulating material, and conductive material so as to protect the HIFU from the heat and to electrically couple conductors to the HIFU transducer 256. In the embodiment of FIG. 2, the HIFU transducer is shown coupled to conductors 258-1 and 258-2 isolated from each other by an insulating coating. The conductors 258-1 and 258-2 extend from the distal end 218 of the catheter 213 to the proximal end 216 and from the proximal end 216 to a signal generator 260 and an amplifier 262 outside the catheter 213. In various embodiments, an electrical signal from the signal generator 260 can be sent along the conductors 258-1 and 258-2, which generates electrical potential across the HIFU transducer 256. The electrical potential causes the HIFU transducer to deform in response to the changing potential and emit HIFU.

In various embodiments, the HIFU transducer 256 can be shaped and positioned in a manner that gives the emitted HIFU directionality. For example, in the embodiment illustrated in FIG. 2, the HIFU transducer has a concave shape and is therefore, able to focus the HIFU in a forward direction to a focal point. As will be discussed herein, the focal point of the HIFU can include tissue of the LAA that is to be fused together. In various embodiments, the HIFU transducer 256 may be made of various materials having piezoelectric characteristics. Example of suitable materials can include, but are not limited to, piezoelectric zirconium titanate (PZT) and polyvinylidene difluoride (PVDF), among others. HIFU can be produced at the focal point by thermal and/or cavitation effects or a combination of thermal and cavitation effects caused by focused application of piezoelectric-generated high-intensity focused ultrasound.

Figure 4:
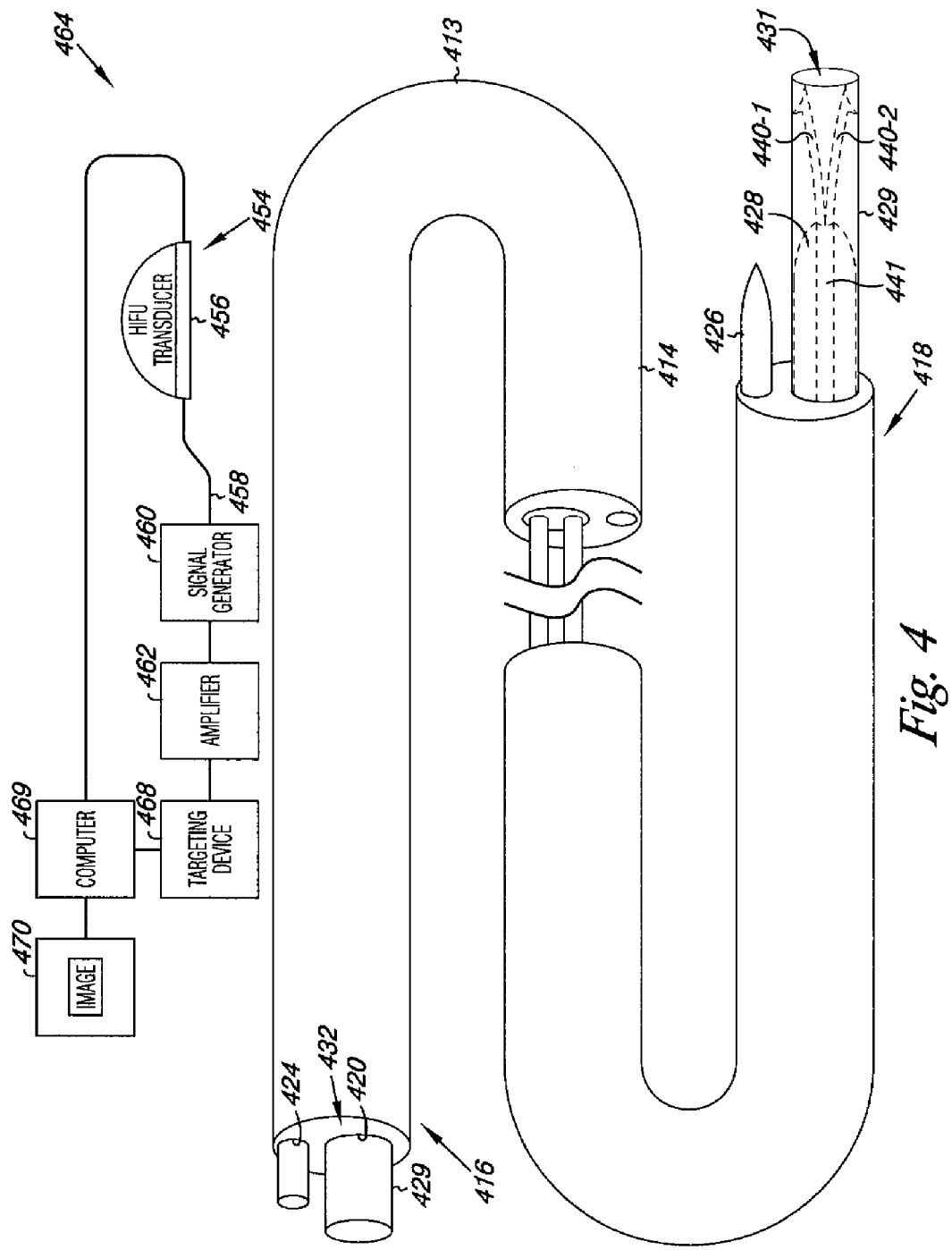
FIG. 4 illustrates an embodiment of a system of the present disclosure.

In various embodiments, the occlusion apparatus can include a targeting device, such as targeting device 468 illustrated and described in FIG. 4. In various embodiments, the targeting device can be physically separate from the occlusion apparatus. In some embodiments, the targeting device can be coupled to the occlusion apparatus. In addition, various components such as processors, circuits, computer executable instructions (e.g., software), etc., can be used in conjunction with the occlusion apparatus 212 and the targeting device, as will also be discussed in more detail below with respect to FIG. 4.

In one embodiment, the targeting device (e.g., 468 in FIG. 4) can be operatively coupled to a portion of the elongate body of catheter. In various embodiments, the targeting device can include a low intensity imaging ultrasound device configured to locate a target and guide the high intensity focused ultrasound to a target from within the human body. The targeting device can be coupled to a signal generator and other hardware configured to provide low intensity imaging ultrasound signals to the imaging ultrasound device. In various embodiments, signal generator 260 can be configured to provide low intensity imaging ultrasound signals. In various embodiments, an electrical signal from the signal generator can be sent along conductors coupled to the low intensity imaging ultrasound device to create a signal potential across a transducer of the low intensity ultrasound imaging device. As discussed above, the signal potential causes the low intensity ultrasound transducer to deform in response to the changing potential and emit low intensity imaging ultrasound signals. The low intensity imaging ultrasound signals can then be processed to create and/or locate a target and provide an image of the target on a display screen, as will be discussed below in FIG. 4.

FIG. 4 illustrates an embodiment of a high intensity focused ultrasound system 464. In various embodiments, the system 464 can include a catheter 413. The catheter 413 includes an elongate body 414 having a proximal end 416 and a distal end 418. The catheter 413 includes lumen 420 extending from the proximal end 416 to the distal end 418 of the catheter 413.

In various embodiments, the system 464 can include the closure sheath 429, as the same has been illustrated and described herein. The closure sheath 429 can be slidably coupled within the first lumen 420 of the elongate body 414, as shown in FIG. 4.

In various embodiments, the system 464 can include a tissue apposition member 428, as the same has been described herein. The tissue apposition member 428 can travel within lumen 431 of closure sheath 429 along the length of the catheter 413 and extend radially from an opening in the catheter 413 at the distal end 418, as shown FIG. 4.

The catheter 413 can further include the guidewire lumen 424. The guidewire lumen 424 can extend within and along the length of the elongate body 414 of the catheter 413 from the proximal end 416 to the distal end 418 of the catheter 413. In various embodiments, the guidewire lumen 424 can receive the guidewire 426 for positioning the catheter 413 and the tissue apposition member 428 within a heart chamber e.g., a left atrium of a patient, as the same has been described herein with respect to FIG. 2. In various embodiments, the guide wire lumen 424 and lumen 420 can include various configurations. For example, in some embodiments, the guidewire lumen 424 and the lumen 420 can include a dual lumen configuration within the catheter 413, as shown in FIG. 4. In other embodiments, the guidewire lumen 424 and lumen 420 can include a coaxial configuration within the catheter 413.

As the reader will appreciate, various components of the system 464 can be operated by directly grasping their proximal ends and manipulating them or in the case where deployment rods are used, by directly grasping the deployment rods to manipulate the components. For example, as shown in the embodiment of FIG. 4, the base 441 of the apposition arms 440-1 and 440-2 extend from the proximal end 416 of the catheter 413, as shown in the embodiment of FIG. 4.

In various embodiments, the system 464 can include an energy emitting device 454. As shown in the embodiment of FIG. 4, the energy emitting device 454 can include a HIFU transducer 456, as the same has been described herein. In the embodiment of FIG. 4, the HIFU transducer 456 is configured to emit HIFU from outside the human body to a target inside the human body. In various embodiments, the HIFU transducer 456 is operatively coupled to conductors 458, a signal generator 460, amplifier 462, a computer 469 including computer executable instructions (e.g., software), a targeting device 468, and a display 470, as shown in the illustration of FIG. 4.

As used herein, the targeting device 468 is a device that can provide, create and/or locate a target to which HIFU emitted from the energy emitting device 343 can be guided, directed, applied, delivered, and the like. As used herein, a target is a location to which an energy emitting device 454 delivers energy, for example, tissues of the LAA. As used herein, locating a target means visually defining a target using the display screen, e.g., 470, to display an image of tissue in which an operator can guide HIFU and/or using program instructions executing on a computer 469 to create a target using trigonometric algorithms (e.g., triangulation), dynamic depth focusing algorithms, etc., to which the HIFU is directed. For example, locating a target can include visually observing an image of the target (e.g., an image of tissue) to which HIFU is to be directed.

In various embodiments, guiding, directing, etc., the HIFU to the target can include utilizing the targeting device 468 in conjunction with program instructions executing on a computer 469 coupled to the targeting device 468 and energy emitting device 454 to help guide the HIFU to the target. In such embodiments, guiding the HIFU to the target can include a manual process where the physician controls the direction of the HIFU, and other parameters such as frequency, intensity, and focus of the HIFU. In some embodiments, the energy emitting device and the targeting device are electrically and communicatively coupled to each other and include program instructions executable to provide automated locating and guiding of the high intensity focused ultrasound to the target. For example, in various embodiments, locating and guiding the HIFU to the target can include an automated process where mechanical devices, such as robotic devices, control the direction of the HIFU including the frequency, intensity, and focus, among other parameters involved in operating the targeting device 468 and the HIFU transducer 456. In such an embodiment, for example, the HIFU transducer 456 can be motorized and electrically and communicatively coupled to the targeting device and other components (e.g., signal generator 260 and amplifier 262, among others).

The targeting device 468 can include a single component or multiple components. In various embodiments, the components of the targeting device 468 can be located at a target, proximal to a target, and/or distal to the target. For example, in some embodiments, the targeting device 468 can include multiple components where one component is located adjacent the target, and another component is located distal to the target. In various embodiments, the targeting device can include radiopaque markers as one component positioned at or proximal to the target along with apposition arms within the human body, as described in FIGS. 3A-3D, and as another component such as a display screen positioned outside the human body to provide an image of the radiopaque markers at or proximal to the target.

Examples of the targeting device 468 and components of the targeting device 468 can include, but are not limited to, imaging probes and devices (e.g., magnetic resonance imaging, ultrasound imaging, optical imaging), Doppler devices (e.g., Doppler audio), software, computers, dynamic depth focusing devices, targeting markers (e.g., ultrasound targeting icons, radiopaque markers), etc. Other devices and components of the targeting device can include echogenic, angioscopic, and fluoroscopic visualization techniques. In some embodiments, the targeting device 468 can include Virtual Reality (VR) systems, and Augmented Reality Systems, where real-time information, such as an image of a PFO from the patient, is integrated with that from a 3-D model of the patient's PFO from a Virtual Reality system. Other visualization devices and systems are also contemplated.

In various embodiments, the targeting device 468 can perform other functions such as monitoring the tissue for physical changes, visual changes, thermal changes, and the like. For example, in various embodiments, an operator of the targeting device 468 can monitor the temperature of the tissues of the LAA after HIFU has been applied to determine if the tissues have sufficiently cooled and whether they have fused together (i.e., renatured). In such embodiments, the targeting device 468 can include a monitoring function that provides thermometric imaging and can produce a temperature map of the targeted area, as the same will be known and understood.

Multiple components can be employed in conjunction with the targeting device 468. For example, catheter 413 can include temperature sensors coupled to the distal end 418 of the catheter 413. In various embodiments, the tissue apposition member 428 can include temperature sensors coupled to the tissue apposition member 428 and/or to the components of the catheter (e.g., apposition arms 440, 440-1, and 440-2). Embodiments are not limited to these examples.

In various embodiments, the targeting device 468 can be located outside the human body. In various embodiments, the targeting device including other components, e.g., program instruction executing on computers, etc., can be used in conjunction with the occlusion apparatus as described in connection with FIGS. 2, and 3A-3D. In various embodiments, the targeting device can create, locate, and/or guide the HIFU emitted from the HIFU transducer 256 coupled to the occlusion apparatus 212 to the target as described in FIG. 2.

The various embodiments of the targeting device can provide real-time images of the target (e.g., via a real-time imaging ultrasound device, a real-time MR imaging device, a real time optical imaging device, etc.). The real-time images can be provided before, during, and/or after the application of energy to the target. For example, in various embodiments, a targeting device that includes a real-time imaging ultrasound device can be configured to provide real-time images of a target, e.g., tissue of an LAA, such that an operator of the energy emitting device can apply energy to the target while simultaneously viewing the target. Such embodiments allow the operator to verify that energy emitted from the energy emitting device is correctly guided to a particular target. Such embodiments also provide the operator with real-time monitoring of changes to tissues induced by the application of energy to the tissues while the energy is being applied to the tissues.

FIGS. 5A-5E illustrate embodiments of methods for fusing tissues of a left atrial appendage by bringing tissues of the LAA together and fusing the tissues with an energy emitting device located outside the human body.

Figure 5A:
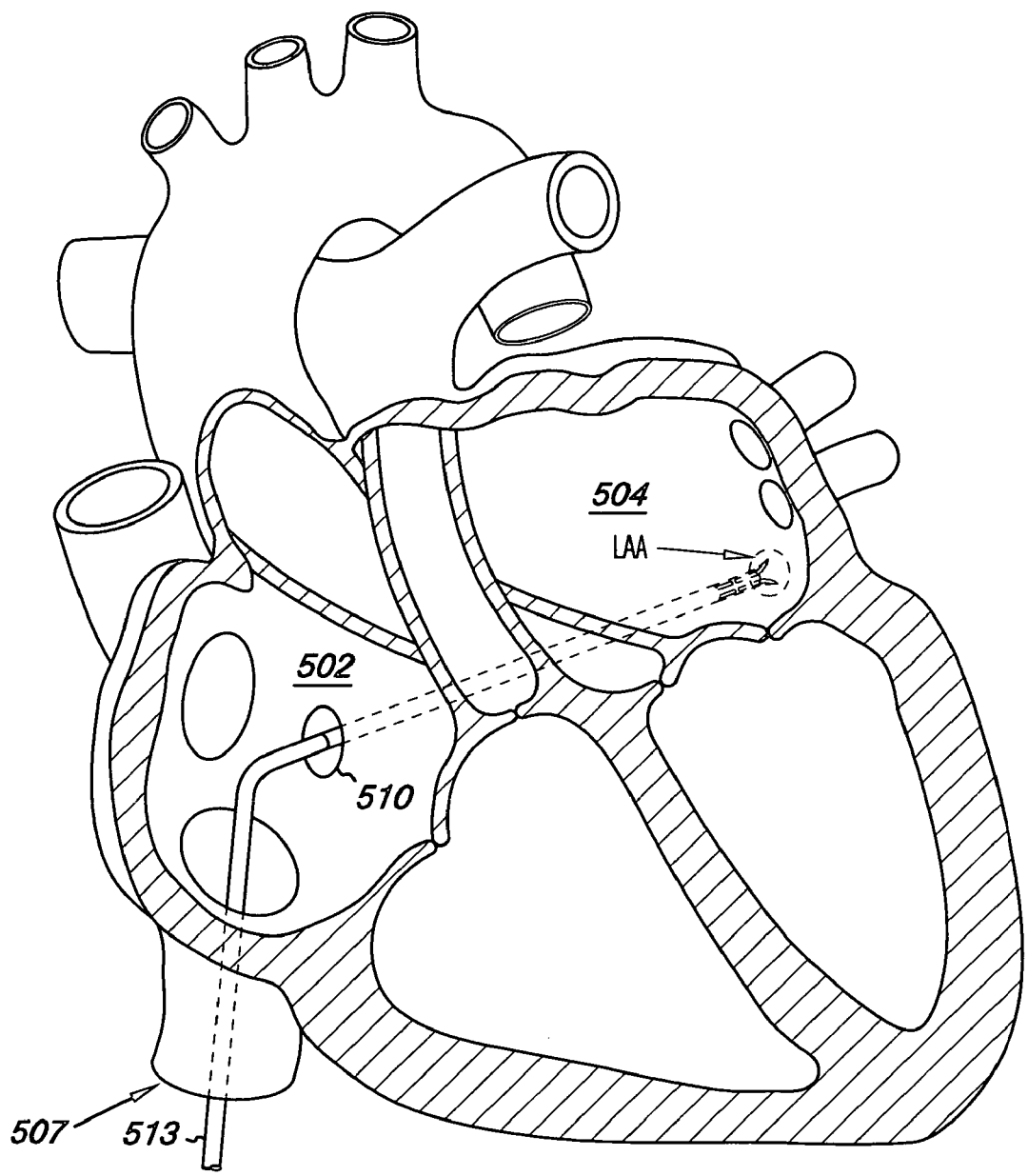
FIG. 5A-5E illustrates various embodiments of a method to fuse tissue of the left atrial appendage.

The LAA can be accessed in a number of ways as will be apparent to those skilled in the art. As shown in the embodiment of FIG. 5A, accessing the left atrium can be accomplished by entering the right atrium and penetrating the fossa ovalis to gain entry to the left atrium. In various embodiments, catheter 513 can be positioned within the right atrium 502 by introducing the catheter 513 into the venous system of the patient using a minimally invasive percutaneous, transluminal catheter based delivery system. For example, a guidewire can be positioned within the venous system and advanced to the right atrium 502 of a patient. In various embodiments, the right atrium 502 can be entered via the orifice of the inferior vena cava 507. The catheter 513 can be positioned over the guidewire and the catheter advanced so as to position the distal end of the catheter at or adjacent the septal wall of right atrium 502. A unique aspect of the fossa ovalis 510 is its location relative to the orifice of the inferior vena cava 507. Since the fossa ovalis 510 is located above and to the left of the orifice of the inferior vena cava 507, the catheter 513 can be immediately advanced to the fossa by the use of the guide wire upon entering the right atrium 502 from the orifice of the inferior vena cava 507. In various embodiments, the targeting device and various components of the targeting device illustrated in FIG. 4 can be utilized to help properly position the catheter within the right atrium 502 and to help locate the fossa ovalis 510. For example, radiopaque markers on the catheter and/or the tissue apposition member can be used to help position the catheter within the right atrium and proximal to or adjacent the fossa ovalis. Radiopaue markers can also be placed on the various components of the catheter (e.g., apposition arms) to help visualize and manipulate the components within the heart. In addition, orientation and visualization of the catheter and its various components, e.g., tissue apposition member and apposition arms may be accomplished through the use of any combination of MR imaging, echogenic, angioscopic, imaging ultrasound and fluoroscopic visualization techniques.

Once the physician has properly positioned the distal end of the catheter adjacent the fossa ovalis 510, the physician can advance the catheter through tissue adjacent to the fossa ovalis 510 to access the left atrium 504. As used herein, the tissue adjacent to the fossa ovalis can be defined by parallel membranes or tissue generally referred to as septum secundum (SS) and septum primum (SP). In some patients, these tissues are fused, and thus, the catheter can be advanced to the left atrium by passing through the fused tissues. In other patients, the SS and SP do not fully fuse and thus, a passage is defined by the SS and SP. In such embodiments, the catheter can be advanced to the left atrium by passing through the passage.

In various embodiments, a radiopaque contrast media may then be injected through a lumen in the guidewire to allow visualization and ensure that the location of the guidewire is in the left atrium, as opposed to other locations, e.g., the aorta. Once the location of the guidewire is confirmed, the catheter can be advanced into the left atrium and to the LAA, as shown in FIG. 5A.

The embodiments of FIGS. 5B-5E illustrates in more detail an operation of the apposition arms 640-1 and 640-2 in helping to bring tissues of the LAA together, i.e., appose tissues of the LAA. The tissue apposition member 528 illustrated in the embodiments of FIGS. 5B-5E include the embodiment of the tissue apposition member illustrated in FIG. 3C. In various embodiments however, the tissue apposition members illustrated in FIGS. 3B-3F can also be used to appose tissues of the LAA.

Figure 5B:
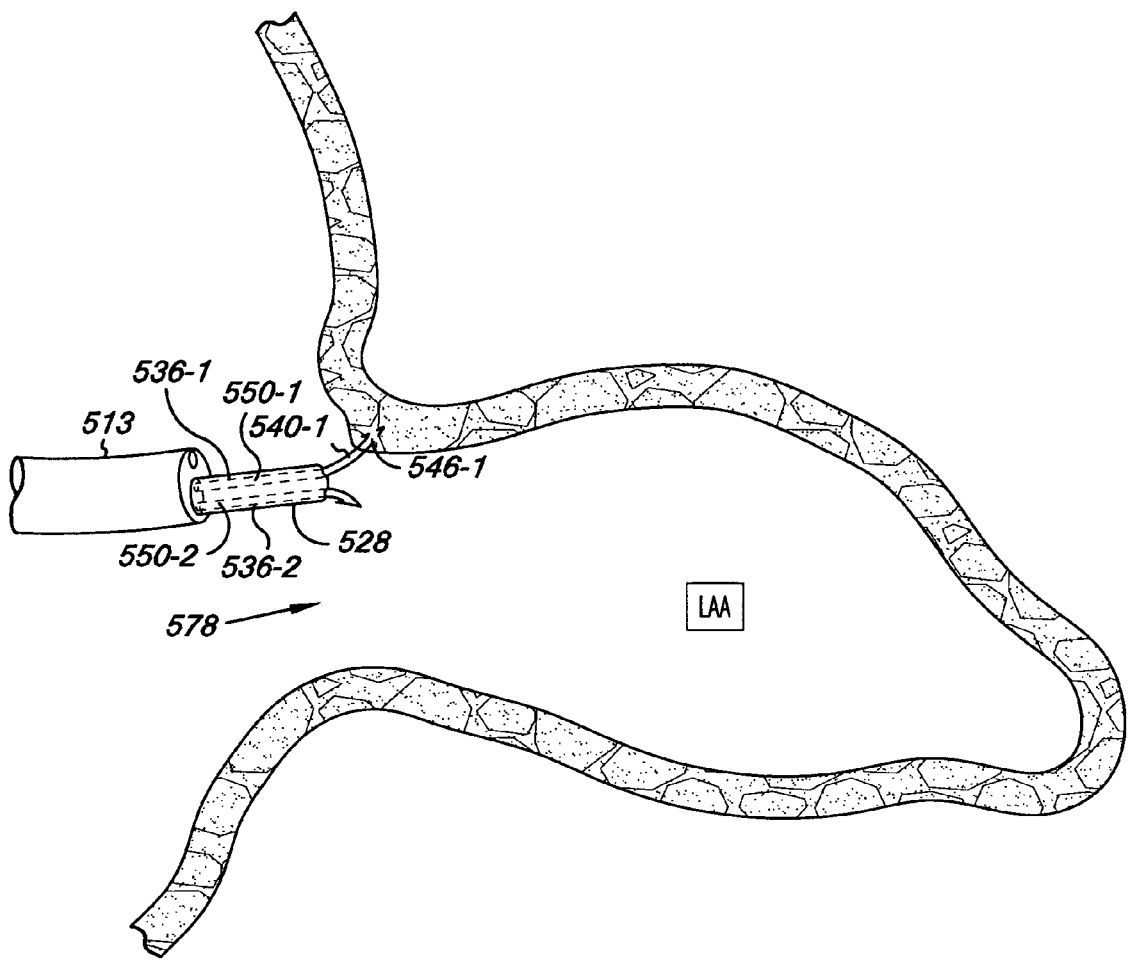
Figure 5C:
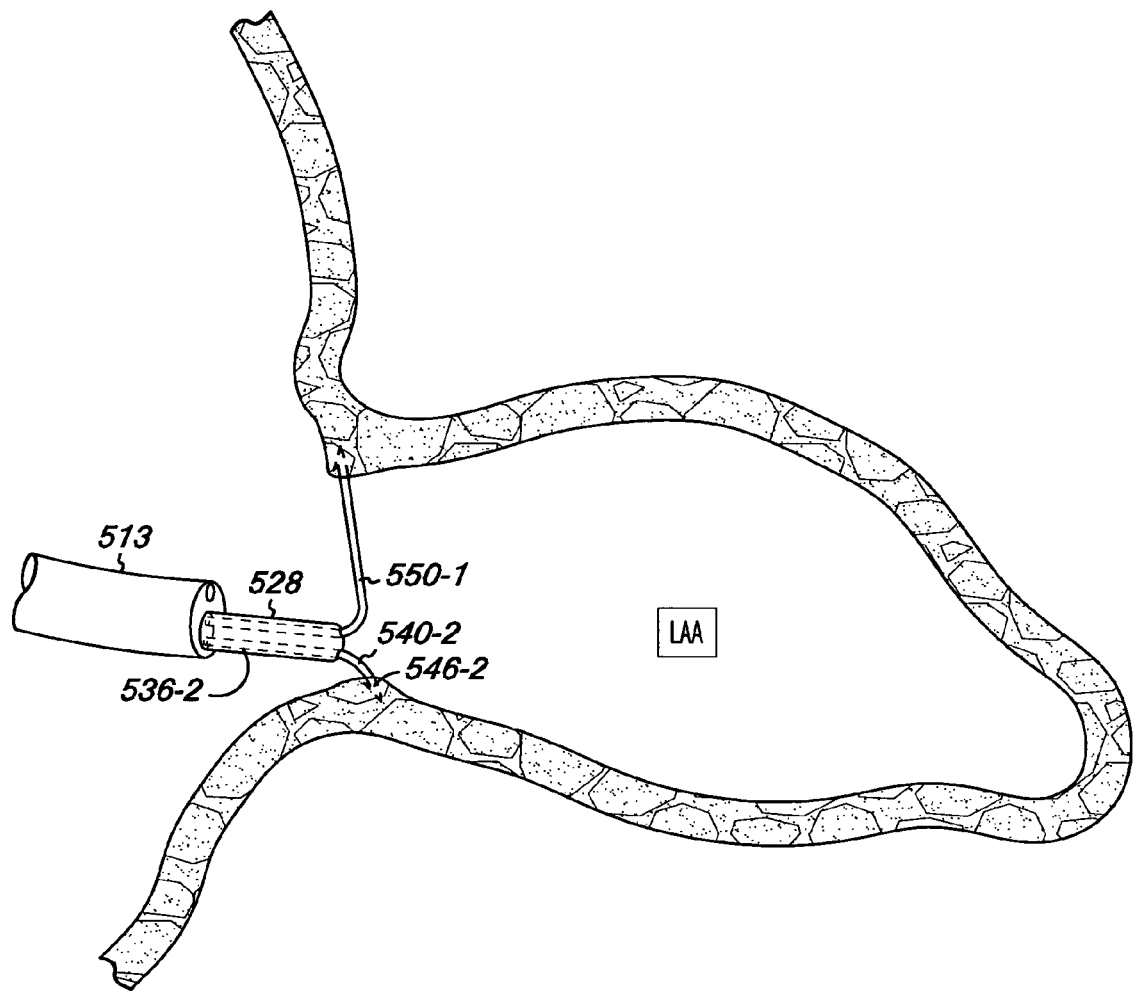

As discussed herein, the first and second apposition arms 540-1 and 540-2 can be manipulated by an operator to help position them adjacent tissues of the LAA. In addition, the first and second apposition arms 540-1 and 540-2 can be manipulated to help bring the tissues of the LAA together. As shown in FIG. 5B, one method for bringing tissues of the LAA together can include extending the distal end 534 of the tissue apposition member 528 from the catheter 513 and positioning the distal end 534 proximal opening 578 of the LAA, as shown in FIG. 5B Once positioned, first and second apposition arms 540-1 and 540-2 can be extended from lumens 536-1 and 536-2 at the distal end 534 of the tissue apposition member 528 using deployment rods 550-1 and 550-2 as shown in FIGS. 5B and 5C. As discussed herein, the apposition arms 540-1 and 540-2 can include a predefined shape designed to pierce and hook the first and second apposition arms 540-1 and 540-2 within the tissues of the LAA so as to lodge the hooking structures 546-1 and 546-2 within the tissues, as shown in FIGS. 5B-5E.

For example, in various embodiments of FIG. 5B, the predefined shape of the first apposition arm 540-1 includes hooking structure 546-1 that can be manipulated by an operator to pierce the tissue of the LAA by forcibly pushing the apposition arm 540-1 using deployment rod 550-1 into the tissue. Once pierced, a barb on the hooking structure catches the tissue and lodges the hooking structure 546-1 within the tissue LAA so as to preclude the first apposition arm 540-1 from backing out of the tissue.

Once the first hooking structure is lodged within the tissue of the LAA, the catheter can be moved to a different location of the LAA, e.g., opposing tissue of the LAA shown in FIG. 5C. Once the catheter 513 is properly positioned proximal to tissue opposing tissue in which the first apposition arm 540-1 is lodged, the second apposition arm 540-2 can be extended from lumen 536-2 of the tissue apposition member 528. The second apposition arm 540-2 can also include the predefined shape. The predefined shape of second apposition arm 540-2 can also be manipulated to pierce the tissue of the LAA when it is extended from the tissue apposition member 528. The predefined shape of the second apposition arm 540-2 includes the hooking structure 546-2 that can be manipulated by an operator to pierce and hook the tissue of the LAA. The hooking structure 546-2 can pierce the tissue of the LAA when a portion of the second apposition arm 540-2 is extended from lumen 536-2 of the tissue apposition member 528 and forcibly pushed into the tissue of the LAA using deployment rod 550-2, as shown in FIG. 5C. As discussed herein with respect to FIGS. 3A-3D, the deployment rods 550-1 and 550-2 can be formed of a resilient material that allows the deployment rods to flex, bend, and rotate. As shown in FIG. 5C, the first deployment rod 550-1 is shown extended from the tissue apposition member 528 in a bent configuration. The resiliency of the deployment rods allow the catheter 513 to move to a different location of the LAA while remaining attached to the apposition arms.

Figure 5D:
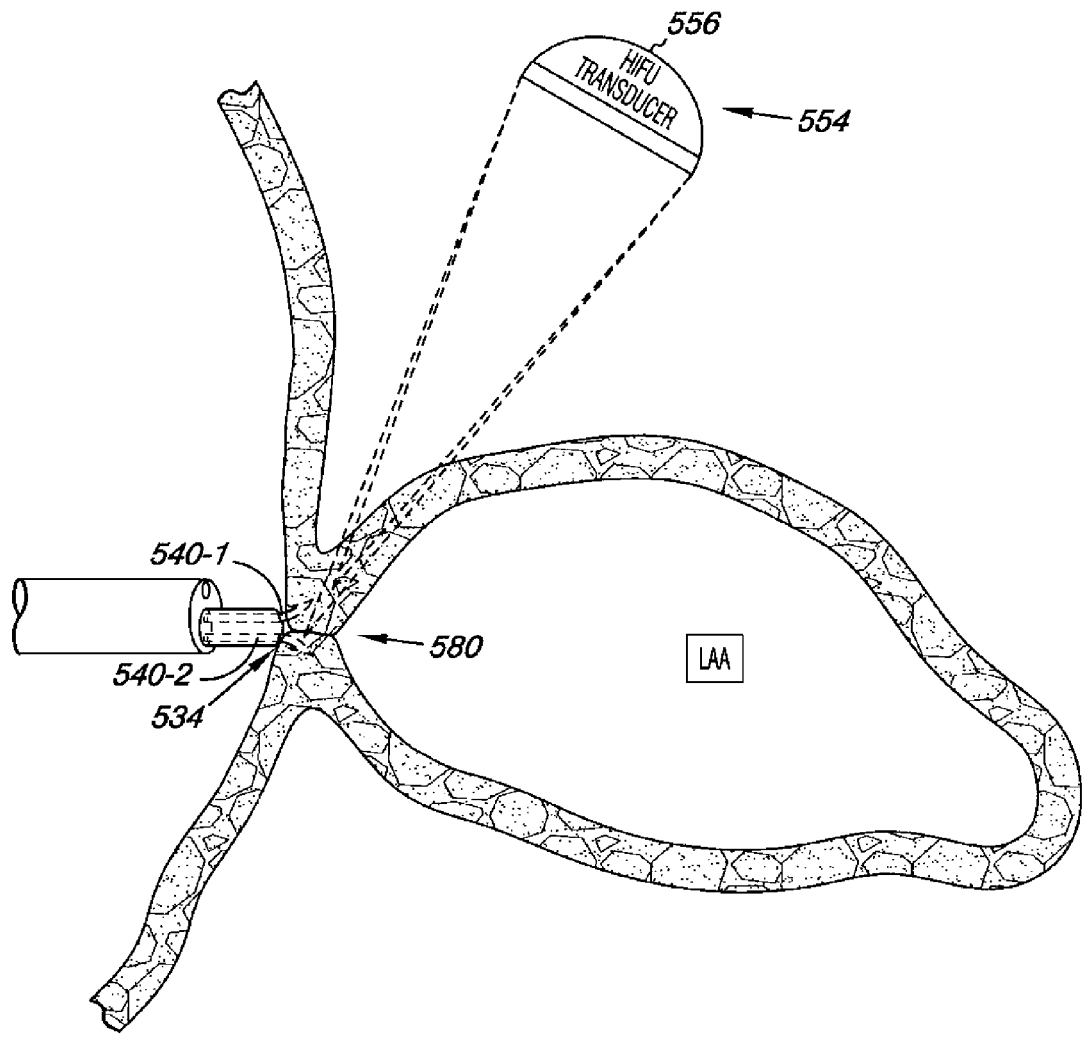

In various embodiments, the pierced tissues can be brought together by further manipulating the first and second apposition arms 540-1 and 540-2 and/or by moving the catheter 513. For example, in various embodiments, an operator can reposition the catheter such that it is positioned an equal distance between the tissues in which the apposition arms 540-1 and 540-2 are lodged. Once repositioned, an operator can apply a pulling force to the apposition arms 540-1 and 540-2 to partially retract a portion of the first and second apposition arms 540-1 and 540-2 into their respective lumens 536-1 and 536-2, as shown in FIGS. 5B, and 5C. As the first apposition arm 540-1 is retracting, the tissue in which the first apposition arm 540-1 is lodged is pulled toward the distal end 534 of the tissue apposition member 528, as shown in FIG. 5D. As the second apposition arm 540-2 is retracting, the tissue in which the second apposition arm 540-2 is lodged is pulled toward the distal end 534 of the tissue apposition member 528, as shown in FIG. 5D. An operator can continue to retract the first and second apposition arms 540-1 and 540-2 until the tissues are brought together so as to contact each other.

In various embodiments, the method for bringing the tissues together can include using a tissue apposition member having the suction arms that can apply a vacuum force to the tissues, as discussed herein with respect to FIG. 3D. For example, the suction arms can be extended from their respective lumens of the tissue apposition member and positioned adjacent tissues of the LAA. In this embodiment, a vacuum force can be applied to the tissues and the suction arms can be retracted in their respective lumens to bring the tissues of the LAA together.

According to various embodiments, the methods for bringing the tissues together can include apposition arms having a predefined shape that includes the grasping structures as described herein with respect to FIG. 3B. For example, the apposition arms can be extended from their respective lumens of the tissue apposition member and positioned adjacent tissues of the LAA. In this embodiment, the grasping structures can be manipulated to grab the tissues of the LAA, as the same will be known and understood by one of ordinary skill in the art. The apposition arms can then be retracted into their respective lumens to bring the tissues of the LAA together.

In various embodiments, the methods for bringing the tissues together can include a single apposition arm having a predefined shape that includes two hooking structures as described herein with respect to FIG. 3C. In this embodiment, the first hooking structure can be used to pierce and hook a first tissue of the LAA and bring it toward a different tissue of the LAA, e.g., an opposing tissue of the LAA. The apposition arm can then be manipulated by an operator to pierce and hook the different tissue with the second hooking structure so as to lodge the second hooking structure within the opposing tissue. Once the two hooking structures have been lodged in opposing tissue of the LAA, an operator can then pull the apposition arm such that a portion of the apposition arm retracts into the lumen of the tissue apposition member. As the apposition arm retracts into the lumen, the portion of the apposition arm that diverges begins to converge as a result of being retracted into lumen. In this embodiment, the convergence of the apposition arm helps to bring the tissues together.

Once the tissues are brought together using any of the methods described above, energy can be applied to the tissues. In various embodiments, the method for fusing tissues of the LAA includes applying energy to tissues with the energy emitting device, as described in connection with FIGS. 2 and 4, to substantially occlude the opening of the LAA.

As described above, applying energy to tissues of the LAA includes applying HIFU to the tissues. For example, in various embodiments, energy emitting device 554 can deliver HIFU to the tissues at the target 580, e.g., the location in which the apposition arms brings the tissues together. In various embodiments, the HIFU transducer can emit HIFU with a frequency in a range of 0.8-15.0 MHz, an intensity in a range of 1,000-10,000 Watt/$cm^2$, and a focus in the range of a 0.75 to 1.25 cm ellipse.

In the embodiment shown in FIG. 5D, the HIFU is indicated by dotted lines originating from the HIFU transducer 556, as described in connection with FIG. 4 (i.e., HIFU emitted from outside the human body to a target located within the human body). As the HIFU approaches the target 580 the HIFU converges until it reaches its focal point, e.g., the apposed tissues. At the focal point, the tissues of the LAA rapidly begin to heat and denature, as discussed herein. The position of the focal point at target 580 relative to the HIFU transducer 556 is a function of the geometry of the HIFU transducer and thus, the focal point can depend, in part, on the location of the HIFU transducer relative to the target 580. As the reader will appreciate, the HIFU transducer embodiment illustrated in FIG. 5D will have a different focal point and thus, a different geometry than a HIFU transducer configured to apply HIFU to the target from within the human body.

As discussed herein, once the tissues are denatured, the tissues begin to renature and fuse together as they cool. In various embodiments, the process can be repeated to fuse the tissue at other targets if the operator so desires. As discussed herein, the targeting device described in FIG. 4, can be used to create, locate, define, etc., the target 580. In addition, the targeting device can be used to guide the HIFU to the target 580 using imaging ultrasound, MR imaging, and other components of the targeting device, as the same have been described herein.

Figure 5E:
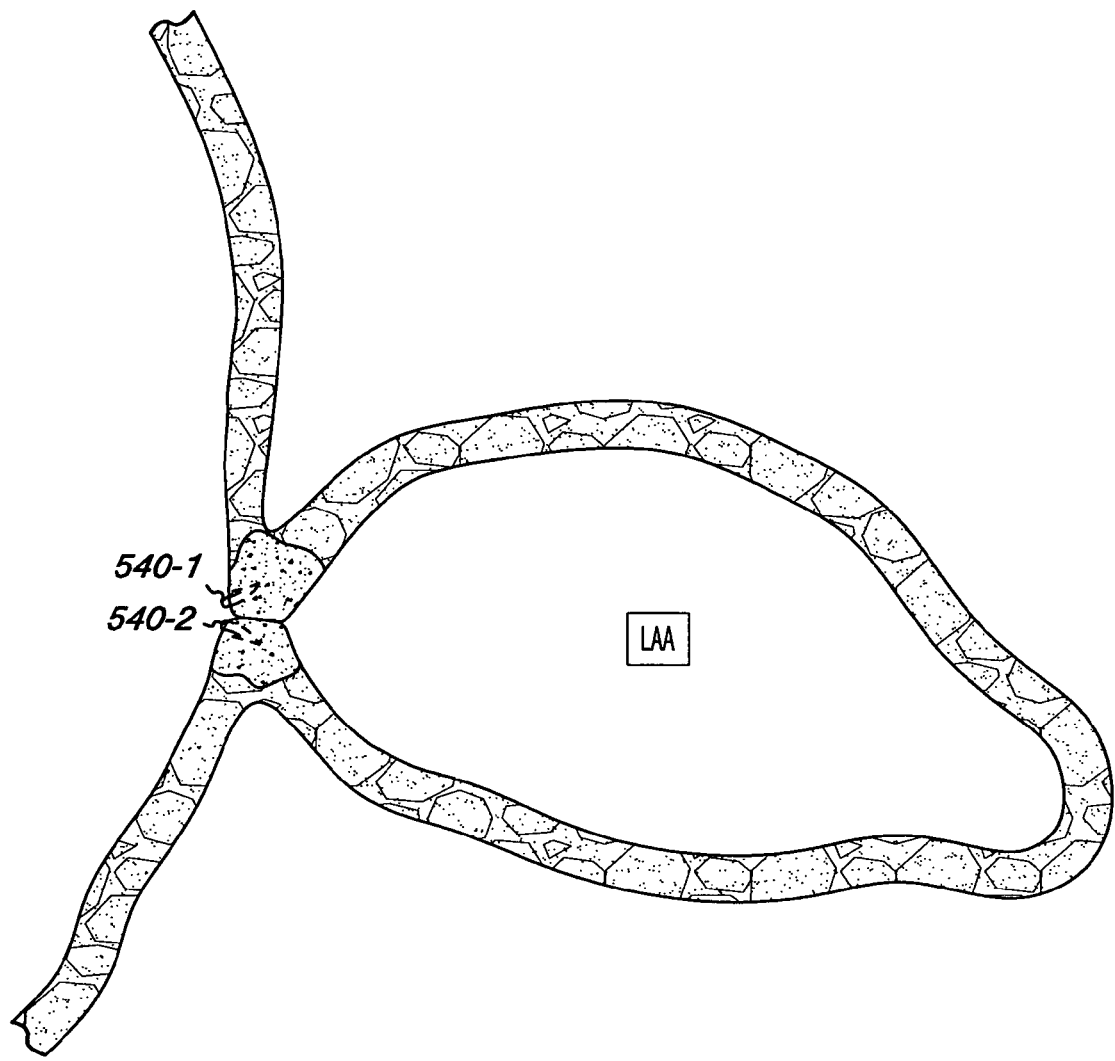

Once the targeted tissues of the LAA are sufficiently denatured, the operator can deactivate the HIFU transducer 556 and wait for the tissues to cool. As discussed herein, when the tissues of the LAA have sufficiently cooled, they begin to renature and fuse together, as shown in FIG. 5E. An operator of the targeting device, as described in connection with FIGS. 2 and 4, can monitor the thick and the thin tissues for changes (e.g., change in temperature) to determine if the tissues have sufficiently cooled and whether they have fused together. When the operator is satisfied that tissues are sufficiently cooled and renatured, e.g., fused together, the operator can release the apposition arms 540-1 and 540-2 from the tissue apposition member by detaching them from the deployment rod, as discussed herein. In these embodiments, once released, the first and second apposition arms 540-1 and 540-2 are left lodged within the tissue of the LAA until they biodegrade and are absorbed by the human body.

Figure 6A:
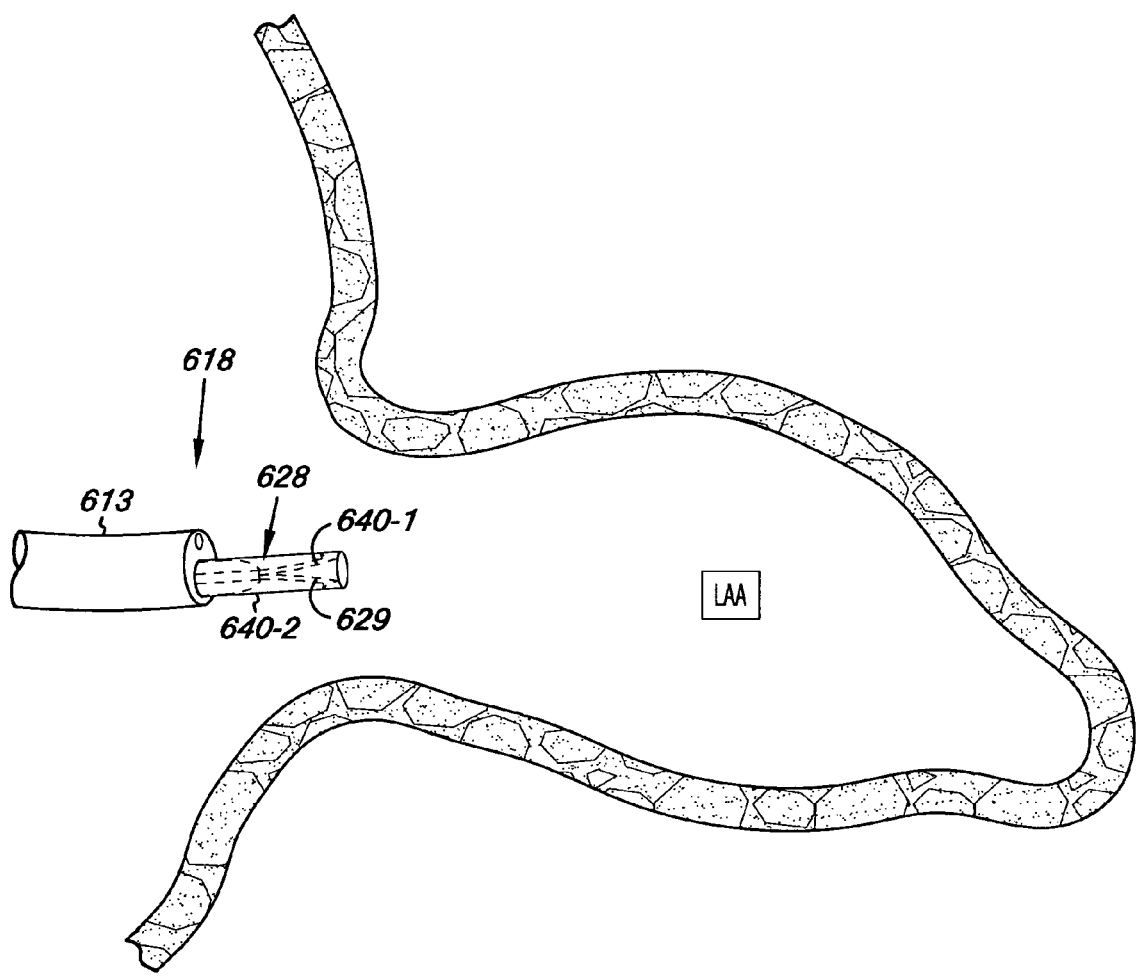
FIGS. 6A-6C illustrates various embodiments of another method to fuse tissue of the left atrial appendage.
Figure 6B:
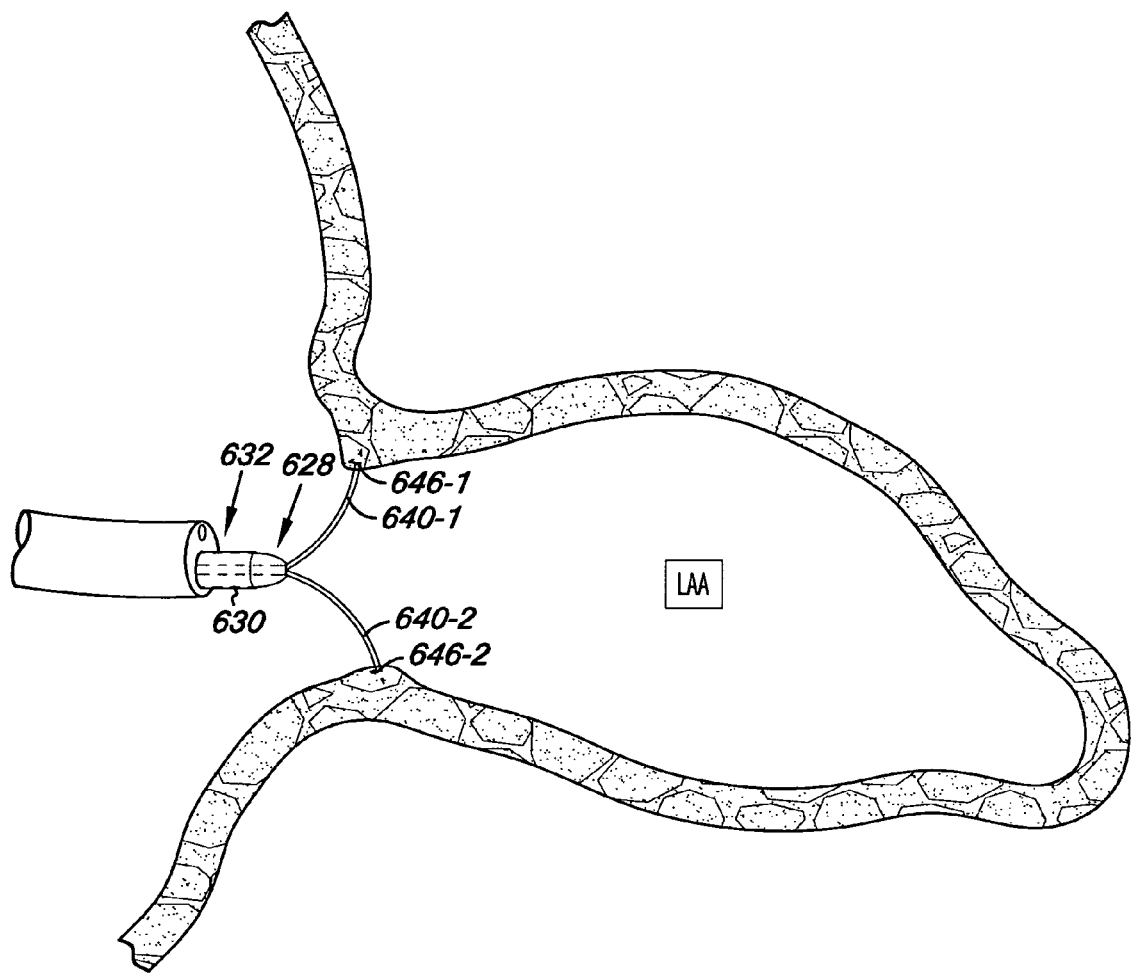
Figure 6C:
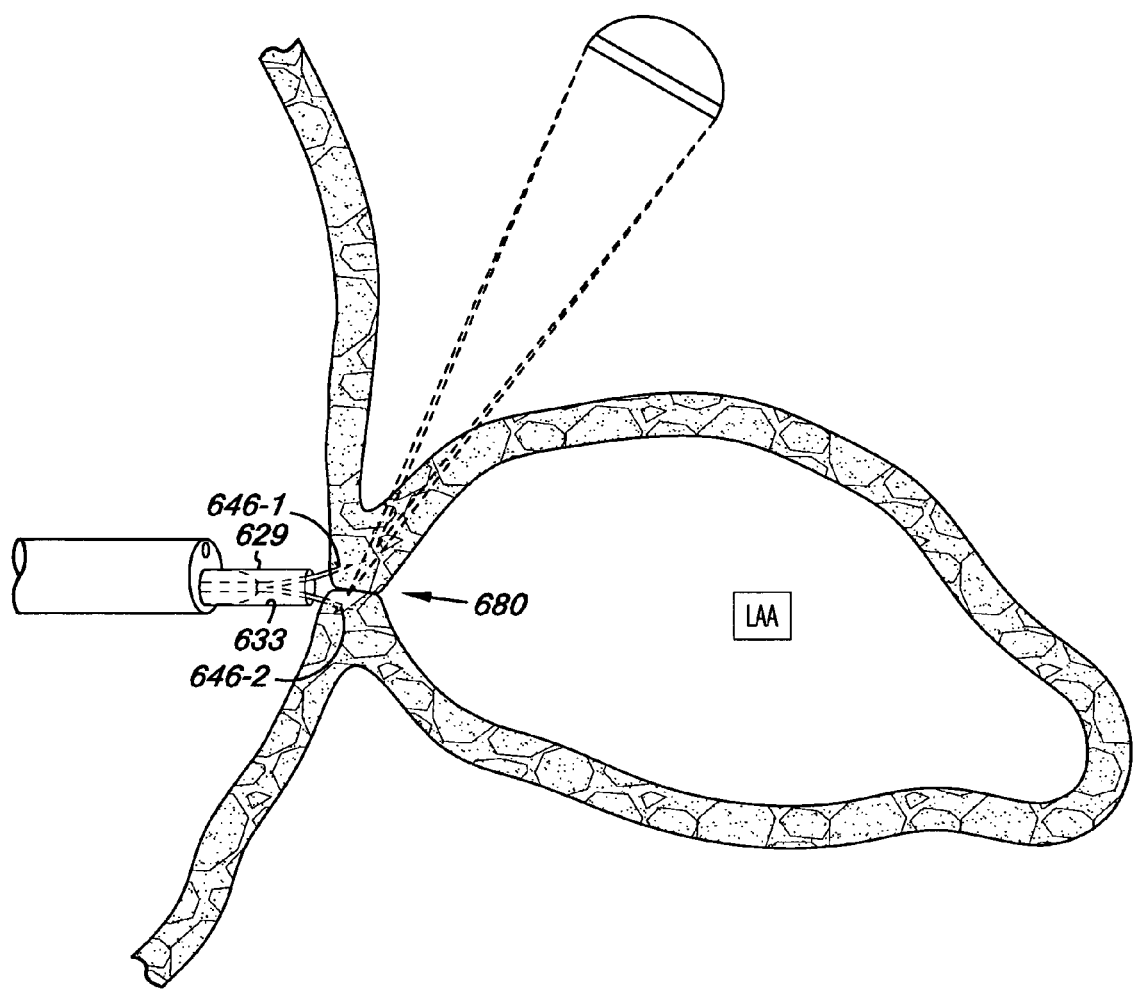

FIGS. 6A-6C illustrate another embodiment of methods for fusing tissues of a left atrial appendage by bringing tissues of the LAA together and fusing the tissues with an energy emitting device located outside the human body.

In various embodiments, the catheter 613 can be advanced to the LAA using the same methods as those described with respect to FIG. 5A. Once the catheter 613 is positioned proximal to the LAA, the distal end 618 of the catheter 613 can be positioned such that the tissue apposition member 628 and the closure sheath 629 are centered relative to the opening of the LAA when those components are extended from the distal end 618 of the catheter 613, as shown in FIG. 6A. As discussed herein, the targeting device and various components of the targeting device discussed with respect to FIG. 4 can be implemented to assure proper positioning and alignment of the catheter 613 and the various components therein.

The embodiments of FIGS. 6B and 6C illustrates in more detail an operation of the apposition arms 540-1 and 540-2 in helping to bring tissues of the LAA together, i.e., appose tissues of the LAA. The tissue apposition member 628 illustrated in the embodiments of FIGS. 6B and 6C include the embodiment of the tissue apposition member 328 illustrated in FIGS. 3E-3G.

Once the distal end 618 of the catheter 613 has been properly positioned, as discussed in FIG. 6A, the closure sheath 629 can be retracted toward the proximal end 632 of the elongate body 630 of the tissue apposition member 628 to release the apposition arms 640-1 and 640-2. As discussed herein with respect to FIGS. 3E and 3F, when the apposition arms 640-1 and 640-2 are released, they spring radially away from the longitudinal axis of the tissue apposition member in opposite directions. As shown in FIG. 6B, the spring like properties of the apposition arms 640-1 and 640-2 engage opposing tissue of the LAA by piercing and hooking the tissue when the apposition arms are released so as to lodge the hooking structures 646-1 and 646-2 within the opposing tissues.

Once the hooking structures have engaged the tissue of the LAA, the closure sheath 629 can be used to draw apposition arms 640-1 and 640-2 together by sliding the closure sheath 629 along the longitudinal axis of the tissue apposition member 628 toward the hooking structures 646-1 and 646-2 as shown in FIG. 6C. In various embodiments, the inner surface 633 of the closure sheath 629 compresses the apposition arms 640-1 and 640-2 toward each other and the engaged tissue with them. In various embodiments, the operator can continue sliding the closure sheath toward the hooking structures until opposing tissue contacts each other. Once the operator is satisfied that the opposing tissues are sufficiently in contact, the operator can lock the closure sheath to preclude the tissues from moving away from each other and apply energy to the tissue (i.e., target 680) with the energy emitting device to substantially occlude the opening of the LAA, as described above in the embodiments of FIGS. 5A and 5E.

While the present disclosure has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An occlusion apparatus, comprising:
    an elongate body having a tissue apposition member extendably positioned within a lumen of the elongate body, the tissue apposition member having a lumen and a first apposition arm and a second apposition arm that diverge from a common base within the lumen of the tissue apposition member, the tissue apposition member to appose tissue of a left atrial appendage (LAA),
    a closure sheath slidably positioned within the lumen of elongate body and along an outer surface of the tissue apposition member, the closure sheath having an opening to allow the tissue apposition member to extend beyond the closure sheath; and
    an energy emitting device coupled to the elongate body, the energy emitting device to emit high intensity focused ultrasound to the tissues to fuse the tissues.

2. The occlusion apparatus of claim 1, where the first and second apposition arms are formed of a shape memory material.

3. The occlusion apparatus of claim 1, where the first and second apposition arms include a predefined shape for hooking and pulling tissue of the LAA.

* * * * *